United States Patent
Hoshino et al.

(10) Patent No.: US 7,550,135 B2
(45) Date of Patent: *Jun. 23, 2009

(54) COMPOSITION FOR EXTERNAL APPLICATION

(75) Inventors: Masahide Hoshino, Haga-gun (JP); Hiroaki Saito, Haga-gun (JP); Yoshiya Sugai, Haga-gun (JP); Mituru Sugiyama, Haga-gun (JP); Yoshinori Nishizawa, Haga-gun (JP); Yasushi Katayama, Sumida-ku (JP)

(73) Assignee: Kao Corporation, Tokyo (JP)

(*) Notice: Subject to any disclaimer, the term of this patent is extended or adjusted under 35 U.S.C. 154(b) by 943 days.

This patent is subject to a terminal disclaimer.

(21) Appl. No.: 10/967,481

(22) Filed: Oct. 19, 2004

(65) Prior Publication Data

US 2005/0112082 A1     May 26, 2005

Related U.S. Application Data

(63) Continuation of application No. 10/082,115, filed on Feb. 26, 2002, now Pat. No. 7,087,646.

(30) Foreign Application Priority Data

Mar. 6, 2001   (JP) .............................. 2001-061695

(51) Int. Cl.
*A61K 8/88* (2006.01)
(52) U.S. Cl. ..................... 424/70.17; 424/70.1; 424/47; 424/401; 514/438
(58) Field of Classification Search ................. 424/401, 424/70.1, 70.17, 47; 514/483
See application file for complete search history.

(56) References Cited

U.S. PATENT DOCUMENTS

| | | | |
|---|---|---|---|
| 4,626,429 A | 12/1986 | Robbins et al. | |
| 5,643,899 A | 7/1997 | Elias et al. | |
| 5,656,668 A | 8/1997 | Motion et al. | |
| 5,753,707 A | 5/1998 | Hoshino et al. | |
| 5,863,945 A | 1/1999 | Murayama et al. | |
| 5,885,955 A | 3/1999 | Uno et al. | |
| 5,932,630 A | 8/1999 | Kovacs et al. | |
| 6,277,361 B1 | 8/2001 | Murray | |
| 6,685,953 B1 | 2/2004 | Hoshino et al. | |
| 2004/0115162 A1 | 6/2004 | Hoshino et al. | |
| 2004/0122103 A1 | 6/2004 | Hoshino et al. | |

FOREIGN PATENT DOCUMENTS

| | | |
|---|---|---|
| DE | 25 15 146 | 10/1976 |
| DE | 36 17 407 | 12/1986 |
| EP | 0 390 986 A1 | 10/1990 |
| EP | 0 805 192 | 11/1997 |
| EP | 1 166 766 | 1/2002 |
| JP | 51-127002 | 11/1976 |
| JP | 4-012825 | 1/1992 |
| JP | 7-507326 | 8/1995 |
| JP | 8-502058 | 3/1996 |
| JP | 8-311003 | 11/1996 |
| JP | 10-218849 | 8/1998 |
| JP | 2001-10946 | 1/2001 |
| WO | WO 96/18391 | 6/1996 |
| WO | WO 00/11125 | 3/2000 |
| WO | WO 00/61097 | 10/2000 |
| WO | WO 01/60387 | 8/2001 |

*Primary Examiner*—Gina C. Yu
(74) *Attorney, Agent, or Firm*—Oblon, Spivak, McClelland, Maier & Neustadt, P.C.

(57) ABSTRACT

The present invention relates to a composition for external application, a humectant and a skin barrier function reinforcing agent, each containing a diamide derivative represented by the following formula (1):

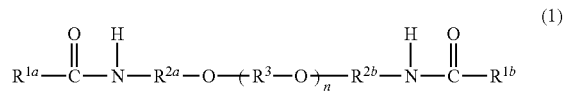

(wherein, $R^{1a}$ and $R^{1b}$ are the same or different and each represents a $C_{1\text{-}23}$ hydrocarbon group, $R^{2a}$ and $R^{2b}$ are the same or different and each represents a divalent $C_{1\text{-}6}$ hydrocarbon group, $R^3$s are the same or different and each represents a divalent $C_{2\text{-}6}$ hydrocarbon group and n stands for 1 to 100).

The composition for external application, humectant and skin barrier function reinforcing agent basically improve the water retaining ability and barrier functions of the horny layer, are excellent in miscibility and mixing stability and can be prepared efficiently at a low cost.

39 Claims, No Drawings

COMPOSITION FOR EXTERNAL APPLICATION

This is a continuation application of U.S. Ser. No. 10/082,115, filed on Feb. 26, 2002 pending.

TECHNICAL FIELD

The present invention relates to compounds capable of maintaining normal barrier functions of the horny layer of the skin and improving its water retaining ability, thereby exhibiting skin roughness lessening effects and the like, and compositions for external application containing these compounds.

BACKGROUND ART

When the water retaining ability or barrier functions of the horny layer are weakened by some internal or external reasons, the skin suffers from various troubles accelerating skin roughness or aging. Lowering in the water retaining ability and barrier functions of the horny layer can also be recognized in the roughened skin resulting from various skin diseases such as atopic dermatitis, psoriasis or xeroderma. Therefore, the maintenance • reinforcement of the water retaining ability and barrier functions of the horny layer are highly important for our healthy daily life.

With the foregoing in view, the present applicants found, as a dermatologic preparation for external application having effects of basically improving (maintaining, reinforcing) the barrier functions of the horny layer, dermatologic preparations for external application containing amide derivatives represented by the below-described formula (2) and applied for a patent (Japanese Patent Laid-Open No. Hei 4-12825).

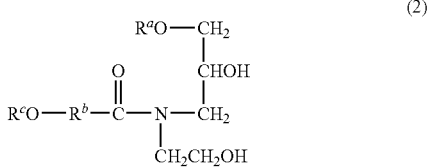
(2)

(wherein, $R^a$ represents a linear or branched, saturated or unsaturated $C_{10-40}$ hydrocarbon group, $R^b$ represents a linear or branched, divalent $C_{3-39}$ hydrocarbon group, and $R^c$ represents a hydrogen atom, a linear or branched, saturated or unsaturated $C_{10-40}$ hydrocarbon group or an acyl group).

Although such amide derivatives bring about excellent effects as described above, their solubility in a base ingredient or stability therewith is not always sufficient. There is therefore a room left for improvement in miscibility or mixing stability of the derivative to be incorporated in a dermatologic preparation for external application. These amide derivatives are accompanied with another problem that necessity of multi-stage reaction upon preparation inevitably leads to a rise in the production cost.

An object of the present invention is to provide a composition for external application which is capable of basically improving the water retaining ability and barrier functions of the horny layer, excellent in miscibility and mixing stability, and available efficiently at a low cost.

DISCLOSURE OF THE INVENTION

The present inventors have carried out a further investigation on amide derivatives. As a result, it has been found that diamide derivatives represented by the below-described formula (1) are effective for reinforcing the water retaining ability of the horny layer and improving the barrier functions of it and at the same time, have excellent miscibility and mixing stability so that they are useful as compositions for external application having preventive • remedial effects for skin troubles such as chapping, and hair protective effects.

In the present invention, there are thus provided compositions for external application, each containing a diamide derivative represented by the following formula (1):

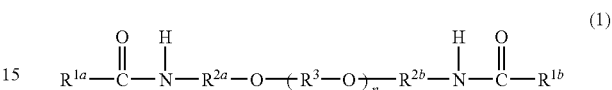
(1)

(wherein, $R^{1a}$ and $R^{1b}$ are the same or different and each represents a $C_{1-23}$ hydrocarbon group, $R^{2a}$ and $R^{2b}$ are the same or different and each represents a divalent $C_{1-6}$ hydrocarbon group, $R^3$s are the same or different and each represents a divalent $C_{2-6}$ hydrocarbon group and n stands for 1 to 100); compositions for external application, each containing said diamide derivative and an intercellular lipid component of the horny layer; and humectants and skin barrier function reinforcing agents each having the diamide derivative as an effective ingredient.

In the present invention, there are also provided a method for reinforcing the water retaining ability of the horny layer and a method for reinforcing the skin barrier functions, each comprising applying an effective amount of said diamide derivative to the skin.

In the present invention, there is also provided a method for relieving excessive hair dryness or improving the touch feel of the hair, which comprising applying an effective amount of said diamide derivative to the hair.

In the present invention, there is also provided the use of said diamide derivative for the preparation of compositions for external application.

In the present invention, there is also provided a diamide derivative represented by the following formula (1'):

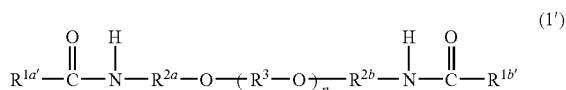
(1')

(wherein, $R^{1a'}$ and $R^{1b'}$ are the same or different and each represents a branched $C_{4-23}$ hydrocarbon group, $R^{2a}$ and $R^{2b}$ are the same or different and each represents a divalent $C_{1-6}$ hydrocarbon group, $R^3$s are the same or different and each represents a divalent $C_{2-6}$ hydrocarbon group and n stands for 1 to 100).

BEST MODE FOR CARRYING OUT THE INVENTION

In the diamide derivative (1) of the present invention, as the $C_{1-23}$ hydrocarbon group represented by $R^{1a}$ and $R^{1b}$, preferred are linear or branched $C_{5-17}$ alkyl or alkenyl groups, with the case wherein $R^{1a}$ and $R^{1b}$ represent the same group being more preferred. Particularly preferred examples of the hydrocarbon group include pentyl, heptyl, nonyl, undecyl, tridecyl, pentadecyl, heptadecyl, 1-ethylheptyl, 2,4,4-trimethylpentyl, 1-heptyldecyl, isoheptadecyl, methyl-branched isoheptadecyl, 8-heptadecenyl and 8,11-heptadecadienyl groups.

The compound represented by the formula (1') wherein $R^{1a}$ and $R^{1b}$ each represents a branched hydrocarbon group having at least 4 carbon atoms is a novel one.

As the divalent $C_{1-6}$ hydrocarbon group represented by $R^{2a}$ and $R^{2b}$, linear or branched $C_{2-6}$ alkylene groups are preferred, with the case wherein $R^{2a}$ and $R^{2b}$ represent the same group being more preferred. Particularly preferred examples of the divalent hydrocarbon group include ethylene, trimethylene, tetramethylene, pentamethylene, hexamethylene, 1-methylethylene and 2-methylethylene groups, of which 1-methylethylene and 2-methylethylene groups are more preferred.

As the divalent $C_{2-6}$ hydrocarbon group represented by $R^3$, linear or branched $C_{2-6}$ alkylene groups are preferred. Of these, ethylene, trimethylene, tetramethylene, pentamethylene, hexamethylene, 1-methylethylene, 2-methylethylene and 2,2-dimethyltrimethylene groups are preferred, with ethylene, 1-methylethylene and 2-methylethylene groups are especially preferred.

Preferably, n stands for 1 to 50, more preferably 1 to 10, with the number less than 4 being especially preferred.

As the diamide derivative (1), compounds of the formula (1) having, in combination, the above-exemplified preferred groups as $R^{1a}$, $R^{1b}$, $R^{2a}$, $R^{2b}$, $R^3$ and n, respectively are preferred. Among them, compounds wherein some or all of the hydrocarbon groups as $R^{1a}$, $R^{1b}$, $R^{2a}$, $R^{2b}$ and $R^3$ are branched are preferred to compounds whose hydrocarbon groups are all linear, because the former ones have a low melting point and therefore have excellent miscibility.

The diamide derivatives (1) to be used for the composition for external application according to the present invention can be prepared by a known amide synthesizing process. It can be prepared efficiently at a low cost, for example, by the below-described process.

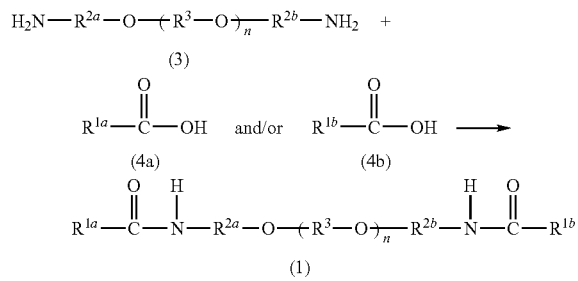

(wherein, $R^{1a}$, $R^{1b}$, $R^{2a}$, $R^{2b}$, $R^3$ and n have the same meanings as described above).

The target diamide derivative (1) is available efficiently by reacting the corresponding diamine (3) with a carboxylic acid (4a) and/or (4b) or reaction derivative (ester, acid halide, acid anhydride or the like) thereof.

The reaction is preferably effected at room temperature to 300° C. under reduced pressure of 1.3 Pa to normal pressure in the presence or absence of a dehydrating agent such as dicyclohexyl carbodiimide or a base, for example, an alkali metal hydroxide such as potassium hydroxide or sodium hydroxide, an alkaline earth metal hydroxide such as calcium hydroxide, an alkali metal carbonate such as potassium carbonate, an alkaline earth metal carbonate such as calcium carbonate, an alkali metal alcoholate such as sodium methoxide, sodium ethoxide or potassium-tert-butoxide, or a tertiary amine such as triethylamine or pyridine. Upon this reaction, the carboxylic acid (4a) and/or (4b) or reaction derivative thereof is preferably used in an excess amount, that is, at least 2 equivalents relative to the diamine (3). Reaction while removing the resulting water out of the system is preferred, because it permits rapid progress of the reaction. The diamide derivative (1) thus available can be purified by the known method such as washing with water, liquid-liquid extraction, column chromatography, distillation, crystallization, recrystallization or pulverization.

Examples of the diamine (3) include polyoxyethylene diamine, polyoxypropylene diamine and polyoxyethyleneoxypropylene diamine, more specifically, polyoxyalkylene diamines "JEFFAMINE" (trade mark, product of HUNTSMAN CORPORATION).

The diamide derivatives (1) of the present invention thus available have effects of maintaining and improving the barrier functions of the skin horny layer and improving water retaining ability of the horny layer so that they are useful as humectants or skin barrier function reinforcing agents. Compositions for external application containing them are effective for remedial effects for skin trouble such as chapping.

In the present invention, use in combination with a water soluble humectant selected from polyhydric alcohols, organic acids or salts thereof, or derivatives thereof and plant extracts makes it possible to synergistically heighten the water retaining ability of the horny layer.

Examples of the polyhydric alcohol include polyglycerins such as glycerin, diglycerin, triglycerin and tetraglycerin, ethylene glycol, 1,3-butylene glycol, 1,4-butylene glycol, propylene glycol, dipropylene glycol, polyethylene glycol, 1,3-propanediol, glucose, maltose, maltitol, sucrose, fructose, xylitol, sorbitol, maltotriose, threitol, erythritol, starch degraded and reduced alcohol, sorbitol, polyoxyalkylene alkyl glucosides. Of these, glycerin, 1,3-butylene glycol, propylene glycol and dipropylene glycol are preferred.

Two or more of these polyhydric alcohols may be used in combination. When they are incorporated in the composition of the present invention for external application in an amount ranging from 0.001 to 50 wt. % (which will hereinafter be called "%", simply), preferably from 0.01 to 40%, especially from 0.1 to 30%, the water retaining ability of the horny layer can be heightened synergistically.

Examples of the organic acid and organic acid derivatives include $C_{2-28}$ oxycarboxylic acids such as glycolic acid, lactic acid, citric acid and 2-hydroxyoctanoic acid, $C_{2-12}$ dicarboxylic acids such as succinic acid, fumaric acid, maleic acid, malonic acid and 1,3-propanedicarboxylic acid, amino acids and derivatives thereof such as aspartic acid, asparagine, glycine, glutamic acid, glutamine, γ-aminobutyric acid, arginine, cysteine and alanine; dicarboxylic monoesters such as octyl succinate and methyl maleate; nicotinic acid or salts thereof, or derivatives thereof such as nicotinic acid, methyl nicotinate, ethyl nicotinate, benzyl nicotinate, nicotinamide, tocopherol nicotinate, quinolinic acid, pyridine-3,5-dicarboxylic acid, nicotinamide adenine dinucleotide phosphate (NADP), nicotinic acid mononucleotide, nicotinyl alcohol and nicotinyl alcohol tartrate; and sterine derivatives represented by the following formula (5):

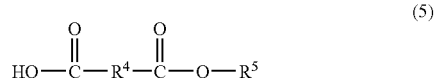

[wherein, $R^4$ represents —$(CH_2)_l$— (l stands for 2 to 10),

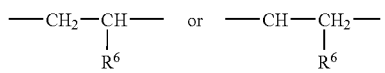

(in which $R^6$ represents a linear or branched $C_{6-20}$ alkyl or alkenyl group), and $R^5$ represents natural sterine or a residue obtained by removing a hydroxyl group proton from the hydrogenated product of the natural sterine].

As the sterine derivative, those of the formula (5) wherein l stands for 2 to 5, $R^6$ represents hexadecenyl or octadecenyl and $R^5$ represents cholesteryl or sitosteryl are preferred.

As the organic acid or organic acid derivative, preferred are α-hydroxycarboxylic acid, amino acid and nicotinic acid and derivatives thereof, with glycolic acid, lactic acid, citric acid, succinic acid, aspartic acid, glycine, arginine, nicotinamide, tocopherol nicotinate and glycine betaine being especially preferred.

Examples of the salt of the organic acid include potassium salt, magnesium salt, calcium salt, aluminum salt and basic amino acid salts of lactic acid, citric acid and succinic acid. When the organic acid has a basic group, examples include acid addition salts of hydrochloric acid, sulfuric acid, nitric acid and phosphoric acid.

At least two of these organic acids or salts thereof, or derivatives thereof may be used in combination. They are preferably incorporated in the invention composition for external application in an amount of 0.0001 to 10%, especially 0.001 to 5%.

As the plant extract, those described in Japanese Patent Laid-Open No. Hei 9-165313 can be mentioned as examples. Of these, especially preferred are extracts, steam distillates or compressed products of eucalyptus, hops, ginger, balloon-flower, GANPIRUNOKI, wild rose, angelica, lily, adlay, cattail, loquat, gardenia, ginseng, soapwort, birch, hydrangea, cloves, safflower, burnet, iris or *Sophora flavewscens*. As an extracting solvent, water, ethanol, 1,3-butylene glycol or the like is usable.

Two or more of these plant extracts may be used in combination. They are preferably incorporated in the composition of the present invention in an amount of 0.0001 to 10%, especially 0.0001 to 5% in terms of a dry solid content.

In the present invention, use in combination of an intercellular lipid component of the horny layer selected from ceramides, pseudoceramides, sphingoglycolipids, sphingophospholipids, sphingosines and derivatives thereof, sphinganines and derivatives thereof, higher fatty acids, cholesterols and derivatives thereof makes it possible to synergistically heighten the barrier functions of the horny layer.

The ceramides include natural ceramides extracted from the brain or skin, followed by purification and synthetic ceramides synthesized by the microbiological or chemical method.

Examples of the natural ceramide include ceramides of Types I to VII, N-oleoyl-sphingosine, N-(12-hydroxyoctade-canoyl)sphingosine, N-(16-hydroxyhexadecanoyl)sphin-gosine and bovine brain ceramide.

As the synthesizing method of a synthetic ceramide, that described, for example, in Japanese Patent Laid-Open No. Sho 59-7118, Japanese Patent Laid-Open No. Hei 4-342553 or WO93/22281 can be employed.

Pseudoceramides can be prepared in accordance with the method described, for example, in Japanese Patent Laid-Open No. Sho 62-228048 or Japanese Patent Laid-Open No. Sho 63-216852. Particularly preferred examples of the pseudoceramide include compounds represented by the following formula (6):

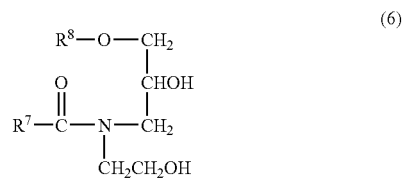

(wherein, $R^7$ represents a $C_{9-17}$ alkyl group and $R^8$ represents a $C_{10-18}$ alkyl group).

Similar to the above-described ceramides, sphingoglycolipids and sphingophospholipids include natural and synthetic ones. Examples of the sphingoglycolipids include those having, as a constituent sugar, glucose, mannose, galactose, glucuronic acid and glucosamine. They also include selebroside and sulfate esters thereof. As the sphingophospholipids, sphingomyelin can be exemplified.

As the sphingosines preferably used in combination, as well as ceramides, pseudoceramides, sphingoglycolipids and sphingophospholipids, preferred are sphingosines disclosed in Japanese Patent Laid-Open No. Hei 5-85924, compounds disclosed in Japanese Patent Laid-Open No. Hei 6-271446 and represented by the formula (7), compounds disclosed in Japanese Patent Laid-Open No. Hei 5-194185 and represented by the formula (8).

Examples of the sphingosines disclosed in Japanese Patent Laid-Open No. Hei 5-85924 include sphingosine (sphingenine), dihydrosphingosine (sphinganine), phytosphingosine, dehydrosphingosine, dehydrophytosphingosine, and sphingadienine and N-methyl derivatives or N,N-dimethyl derivatives thereof. The hydrocarbon group of these compounds preferably has 12 to 24 carbon atoms and it may be either linear or branched, and either saturated or unsaturated.

The compound (7) disclosed in Japanese Patent Laid-Open No. Hei 6-271446 is represented by the following formula:

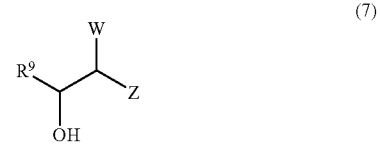

(wherein, $R^9$ represents a $C_{1-40}$ hydrocarbon group which may have a hydroxyl group, Z represents —$CH_2OH$, —$CO_2H$ or

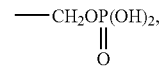

and W represents —$NH_2$, —$NHCH_3$, —$N(CH_3)_2$ or —$N^+(CH_3)_3$).

The compound (8) disclosed in Japanese Patent Laid-Open No. Hei 5-194185 is represented by the following formula:

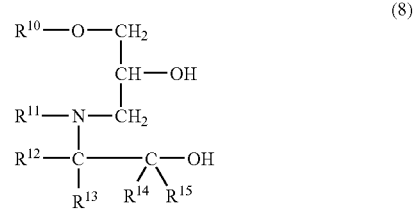

(wherein, $R^{10}$ represents a linear, branched or cyclic, saturated or unsaturated $C_{4-40}$ hydrocarbon group, $R^{11}$, $R^{12}$, $R^{13}$, $R^{14}$ and $R^{15}$ each independently represents a hydrogen atom or a $C_{1-10}$ hydrocarbon group which may be substituted by at least one hydroxyl group).

As the higher fatty acid, those having 12 or more carbon atoms are preferred, with those having 12 to 24 carbon atoms being especially preferred. Specific examples include myristic acid, palmitic acid, palmitoleic acid, stearic acid, oleic acid, linoleic acid and behenic acid. Monoglycerides, diglycerides or triglycerides rich in such a higher fatty acid may be incorporated.

As the cholesterol ester, those composed of a higher fatty acid having 12 or more carbon atoms, especially 12 to 24 carbon atoms are preferred. Specific examples include cholesteryl palmitate, cholesteryl isostearate, di(cholesterol, 2-octyldodecyl) N-lauroyl-L-glutamate, lanoline fatty acid cholesterol and macadamia nut oil fatty acid cholesterol.

Two or more of these intercellular lipid components of the horny layer may be used in combination. They may be incorporated in the composition of the present invention preferably in an amount of 0.001 to 20%, especially 0.005 to 10%.

The content of the diamide derivative (1) in the composition of the present invention is preferably 0.001 to 50% of the whole composition when the composition is an emulsion type dermatologic preparation for topical application. It is preferably 0.01 to 50% of the whole composition when the composition is an oily type dermatologic external preparation containing a liquid hydrocarbon such as squalane as a base ingredient. In either case, addition of it in an amount of 0.01 to 20% is especially preferred. Particularly for the prevention or remedy of skin roughness, addition of it in an amount of 0.1 to 20% is preferred.

The composition for external application according to the present invention can be classified roughly, from the viewpoint of its type of usage, into a medicinal dermatologic external preparation and a cosmetic composition. It is preferred to use as a cosmetic composition, in particular as a cosmetics for skin.

As the medicinal dermatologic external preparation, various ointments containing a pharmaceutically effective ingredient can be mentioned by way of example. As the ointment, either one of an ointment having an oily base or a water-in-oil or an ointment having an oil-in-water emulsion base can be used. Examples of the oily base include vegetable oils, animal oils, synthetic oils, fatty acids, natural and synthetic glycerides and the like. As the pharmaceutically effective ingredient, an analgesic anti-inflammatory agent, antipruritic, disinfectant antiseptic, astringent, skin softening agent, hormone or the like can be used, for example, as needed.

When used as a cosmetic composition (including skin cosmetic composition and hair cosmetic composition), on the other hand, generally-employed cosmetic ingredients such as oily ingredient, surfactant, humectant, ultraviolet absorber, whitening agent, wrinkle remedy, alcohol, chelating agent, pH regulator, antiseptic, thickener, colorant and perfume can be added in any combination to the diamide derivative (1) which is an essential ingredient.

As a cosmetic composition, it is possible to use it in various forms such as water-in-oil or oil-in-water emulsified cosmetic composition, cream, milky lotion, skin lotion, oily cosmetic composition, lip stick, foundation, bath agent, skin cleanser, nail care agent, and hair cosmetic compositions. Specific examples of the hair cosmetic compositions include hair tonic, hair dressing, hair rinse, hair treatment, hair conditioner, hair styling agent, shampoo, baldness remedy and hair growth accelerator.

In the medicinal dermatologic external composition or skin cosmetic composition among the compositions for external application according to the present invention, surfactants such as anionic surfactants, cationic surfactants, nonionic surfactants and amphoteric surfactants can be incorporated. Of these, nonionic surfactants such as polyoxyethylene alkyl ethers, polyoxyethylene fatty acid esters, sorbitan fatty acid esters, polyoxyethylene sorbitan fatty acid esters, fatty acid monoglycerides and glyceryl ether are preferred. The surfactant is preferably added in an amount of 0.01 to 20%, especially 0.1 to 10%, based on the composition.

When the composition of the present invention is used as a hair cosmetic composition, the diamide derivative (1) is preferably added in an amount of 0.001 to 5% for shampoo or the like, 0.1 to 20% for rinse, treatment, conditioner, styling agent or the like, and 0.01 to 5% for hair liquid, hair tonic or the like.

In the hair cosmetic composition, surfactants such as anionic surfactants, cationic surfactants, nonionic surfactants and amphoteric surfactants and ingredients ordinarily employed for hair cosmetic compositions can be incorporated. When the hair cosmetic composition is a shampoo, an anionic surfactant such as alkyl ether sulfate, alkyl sulfate or olefin sulfonate salt can be incorporated as a main surfactant. Its content is preferably 5 to 30% in the composition, with 10 to 20% being especially preferred.

When the cosmetic composition of the present invention is a hair rinse, conditioner, hair treatment or hair styling agent, a cationic surfactant such as mono- or di-(longer chain)alkyl quaternary ammonium salt, a nonionic surfactant such as polyoxyethylene alkyl or alkenyl ether, or an oil or fat such as liquid paraffin can be incorporated in order to impart the hair with good touch feel. The cationic and nonionic surfactants are preferably added in an amount of 0.1 to 50%, especially 0.5 to 20% in the composition.

When the hair cosmetic composition is a hair liquid, hair tonic or the like, a nonionic surfactant such as polyoxyethylene can be incorporated in it. The nonionic surfactant is preferably added in an amount of 0.01 to 20%, especially 0.1 to 5% in the whole composition.

EXAMPLES

Preparation Example 1

Preparation of Compound (A)

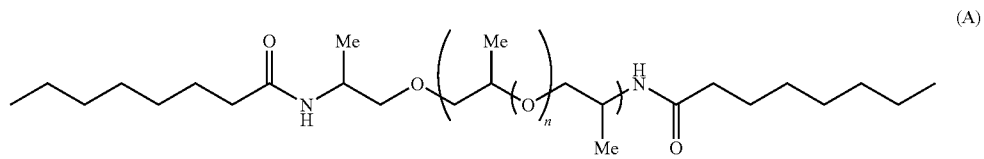

(A)

Average n = 1.7

In a flask equipped with a stirrer, a nitrogen inlet tube and a distillation apparatus, 317 g of caprylic acid ("LUNAC 8-98(E)", product of Kao Corp.) was charged, followed by dropwise addition of 228 g of "JEFFAMINE D-230" (product of Huntsman Corp.) over 2.5 hours at 220° C. under stirring in a nitrogen gas stream. Under the same conditions, the reaction mixture was matured for 5 hours. The dropwise addition and maturation were conducted under a nitrogen gas stream, made it possible to conduct them while distilling off the water byproduced. After completion of the reaction, the reaction mixture was subjected to molecular distillation (160 to 210° C., 0.5 Pa), whereby 262 g of the title compound (A) was obtained. The resulting Compound (A) has physical properties as follows:

Colorless Oil $^1$H-NMR (CDCl$_3$, δ): 0.80-1.00 (m), 1.00-1.50 (m), 1.50-1.80 (m), 2.13 (t,J=7.5 Hz), 3.00-3.75 (m), 4.00-4.30 (m), 5.60-6.10 (m).

Preparation Examples 2 to 11

In a similar manner to Preparation Example 1 except for the use of the compounds shown in Table 1 instead of Diamine (3) and Carboxylic acid (4a) or (4b), the below-described Compounds (B)-(k) were prepared. The physical properties of each of the diamide derivatives are also shown in Table 1 and Table 2.

(B)

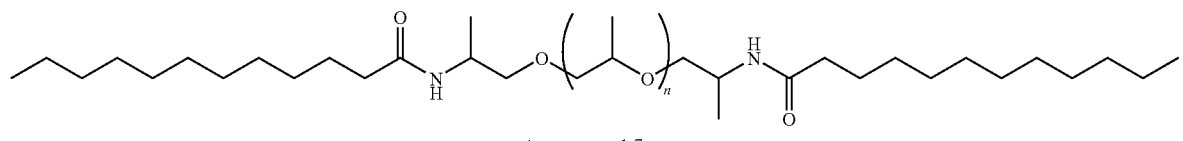

Average n = 1.7

(C)

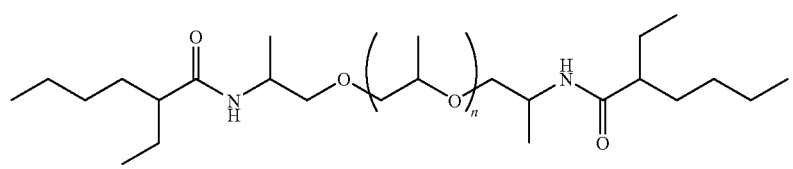

Average n = 1.7

(D)

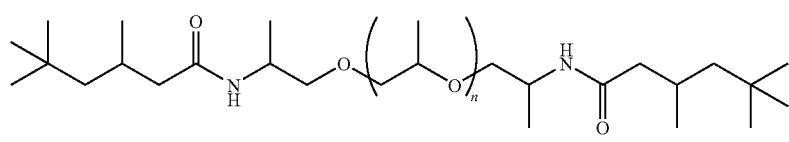

Average n = 1.7

(E)

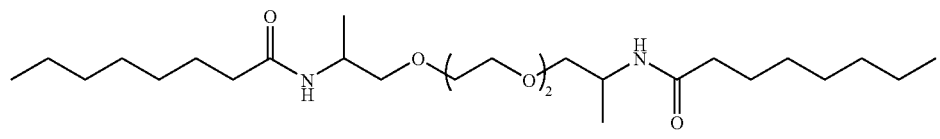

Average structure (F)

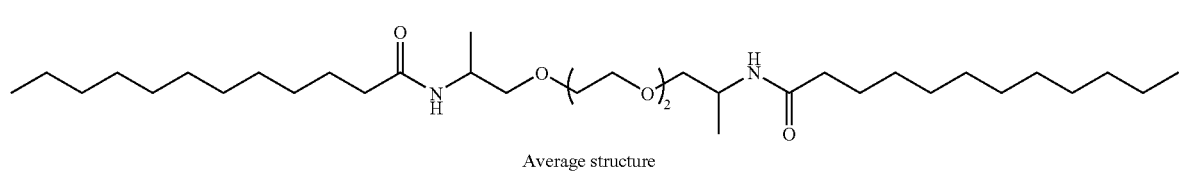

Average structure (G)

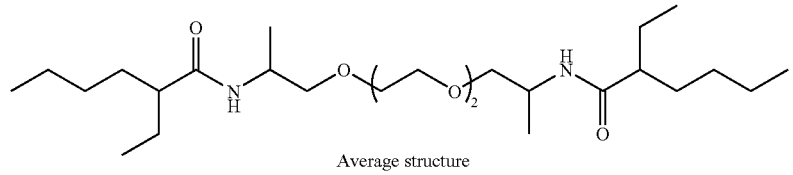

Average structure

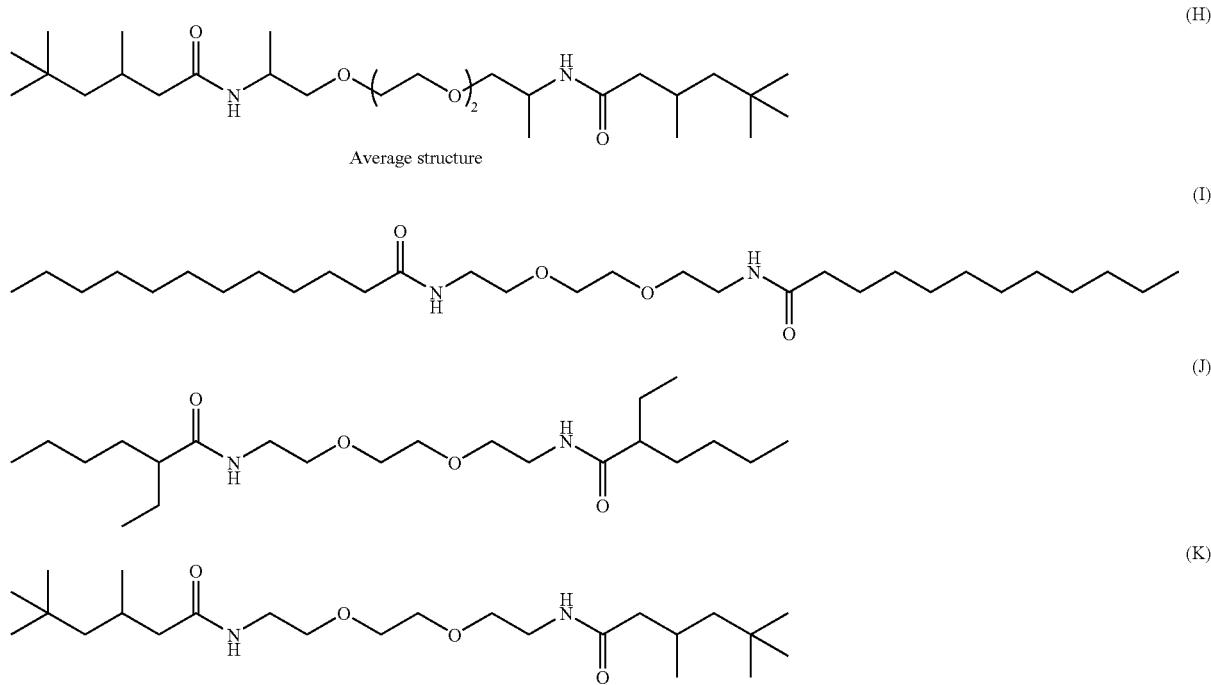

TABLE 1

| | Diamide derivative (1) | Diamine (3) | Carboxylic acid (4a or 4b) | Physical properties |
|---|---|---|---|---|
| Prep. Ex. 2 | Compound (B) | JEFFAMINE D-230 | Lauric acid | White solid, melting point: 74° C. $^1$H-NMR(CDCl$_3$, δ): 0.80- 1.00(m), 1.00- 1.50 (m), 1.50- 1.80(m), 2.13(t, J=7.5Hz), 3.00- 3.75(m), 4.00- 4.30(m), 5.60- 6.10(m) |
| Prep. Ex. 3 | Compound (C) | JEFFAMINE D-230 | 2-Ethylhexanoic acid | Colorless oil $^1$H-NMR(CDCl$_3$, δ): 0.80- 10.5(m), 1.05- 1.75 (m), 1.75- 2.20(m), 3.30- 3.75(m), 4.10- 4.30(m), 5.50- 6.00(m). |
| Prep. Ex. 4 | Compound (D) | JEFFAMINE D-230 | 3,5,5-Trimethylhexanoic acid | Colorless oil $^1$H-NMR(CDCl$_3$, δ): 0.88(s), 0.94(d, J=6.2Hz), 1.00- 1.35(m), 1.85- 2.25 (m), 3.30- 3.70(m), 4.00- 4.30(m), 5.50- 6.20(m). |
| Prep. Ex. 5 | Compound (E) | JEFFAMINE XFJ-511 (polyoxyethylene-oxypropylene diamine, product of HUNTSMAN CORP) | Octanoic acid | Colorless oil $^1$H-NMR(CDCl$_3$, δ): 0.75- 1.00(m), 1.00- 1.45 (m), 1.45- 1.75(m), 2.11(t, J=7.6Hz), 3.35- 3.75(m) 3.42(d, J=4.3Hz), 4.00- 4.30 (m), 5.60- 6.30(m). |
| Prep. Ex. 6 | Compound (F) | JEFFAMINE XFJ-511 | Lauric acid | White solid, Melting point: 61° C. $^1$H-NMR(CDCl$_3$, δ): 0.75- 1.00(m), 1.00- 1.45 (m), 1.45- 1.75(m), 2.14(t, J=7.6Hz), 3.40- 3.70(m), 3.42(d, J=4.3Hz), 4.00- 4.30 (m), 5.60- 6.20(m). |
| Prep. Ex. 7 | Compound (G) | JEFFAMINE XFJ-511 | 2-Ethylhexanoic acid | Colorless oil $^1$H-NMR(CDCl$_3$, δ): 0.75- 1.00(m), 1.00- 1.75 (m), 1.75- 2.00(m), 3.40- 3.70(m), 3.40(d, J=4.4Hz), 4.05- 4.35(m), 5.50- 6.20 (m). |
| Prep. Ex. 8 | Compound (H) | JEFFAMINE XFJ-511 | 3,5,5-Trimethylhexanoic acid | Colorless oil $^1$H-NMR(CDCl$_3$, δ): 0.87(s), 0.93(d, J=6.4HZ), 1.00- 1.35(m), 1.80- 2.25 (m), 3.42(d, J=4.3Hz), 3.50- 3.70(m), 4.00- 4.30(m), 5.55- 6.25(m). |

TABLE 2

| | Diamide derivative (1) | Diamine (3) | Carboxylic acid (4a or 4b) | Physical properties |
|---|---|---|---|---|
| Prep. Ex. 9 | Compound (I) | JEFFAMINE EDR-148 (polyoxyethylene diamine; product of HUNTSMAN CORP) | Lauric acid | White solid, melting point: 116° C. $^1$H-NMR(CDCl$_3$, δ): 0.85(t, J=6.4H, 6H), 1.10- 1.40(m, 32H), 1.50- 1.70(m, 4H), 2.15(t, J=7.6Hz, 4H), 3.45(t, J=5.3Hz, 4H), 3.50- 3.65(m, 4H), 3.59(s, 4H), 5.80- 6.00 (m, 2H). |
| Prep. Ex. 10 | Compound (J) | JEFFAMINE EDR-148 | 2-Ethylhexanoic acid | White solid, melting point: 91° C. $^1$H-NMR(CDCl$_3$, δ): 0.75- 1.05(m, 12H), 1.10- 1.75(m, 16H), 1.75- 2.05(m, 2H), 3.40- 3.65 (m, 8H), 3.59(s, 4H), 5.80- 6.00(m, 2H) |
| Prep. Ex. 11 | Compound (K) | JEFFAMINE EDR-148 | 3,5,5-Trimethylhexanoic acid | Colorless oil $^1$H-NMR(CDCl$_3$, δ): 0.87(s, 12H), 0.93(d, J=6.3Hz, 6H), 1.06(dd, J=6.1, 14.0Hz, 2H), 1.21(dd, J=3.6, 14.0Hz, 2H), 1.90(dd, J=7.5, 12.2Hz, 2H), 1.95- 2.15(m, 2H), 2.17(dd, J=5.1H, 14.0Hz, 2H), 3.40- 3.65 (m, 8H), 3.58(s, 4H), 5.85- 6.00(m, 2H) |

Test 1

Compositions for external application according to the present invention (invention products) containing the diamide derivatives prepared in Preparation Examples 1 to 11 and having the compositions as shown in Tables 3 to 5 were prepared and their percutaneous water transpiration amount and percutaneous absorption amount were measured and evaluated by the methods described below.

(Testing Method)

Male Wister rats were raised using only feed free of essential fatty acids. Those rats showing symptoms of essential fatty acid deficiency were used for the test. After the back of each rat suffering from the essential fatty acid deficiency was shaved thoroughly, the composition for external application was applied to the shaved part once a day for 12 days. A group consisting of five rats was tested for each composition to be evaluated. Three days after completion of the application, the below-described items of the compositions were measured and evaluated.

(1) Percutaneous Water Transpiration

The water transpiration amount from the skin of the back of each rat was measured by TEVAMETER, and inhibitory effects on percutaneous water transpiration were found by the below-described formula:

Degree of percutaneous water transpiration inhibition by the invention product=Percutaneous water transpiration amount of the rat to which Comparative Product 1 has been applied−percutaneous water transpiration amount of the rat to which the invention product has been applied (g/m$^2$/hr).

(2) Percutaneous Absorption

The dorsal skin of the test rat was cut off and fixed on a percutaneous absorption chamber with the epidermis side up. The lower receiver was filled with a phosphate buffer solution. Onto the epidermis, a phosphate buffer solution containing $^{14}$C-salicylic acid of 37 KBq was added, which was then allowed to stand. Nineteen hours later, a fixed amount of the phosphate buffer solution was drawn from the lower receiver and the radioactivity of the $^{14}$C-salicylic acid penetrated into the solution was measured. In accordance with the below-described formula, percutaneous absorption inhibitory effects were determined.

Degree of percutaneous absorption inhibition of the invention product=percutaneous absorption amount of the rat to which Comparative Product 1 has been applied−percutaneous absorption amount of the rat to which the invention product has been applied (dpm)

TABLE 3

| Composition (%) | Invention product 1 | Invention product 2 | Invention product 3 | Invention product 4 |
|---|---|---|---|---|
| Compound (A) | 10 | — | — | — |
| Compound (B) | — | 10 | — | — |
| Compound (C) | — | — | 10 | — |
| Compound (D) | — | — | — | 10 |
| 1,3-Butylene glycol | 62.9 | 62.9 | 62.9 | 62.9 |
| Ethanol | 27 | 27 | 27 | 27 |
| Isostearyl glyceryl ether | 0.1 | 0.1 | 0.1 | 0.1 |

TABLE 4

| Composition (%) | Invention product 5 | Invention product 6 | Invention product 7 | Invention product 8 |
|---|---|---|---|---|
| Compound (E) | 10 | — | — | — |
| Compound (F) | — | 10 | — | — |
| Compound (G) | — | — | 10 | — |
| Compound (H) | — | — | — | 10 |
| 1,3-Butylene glycol | 62.9 | 62.9 | 62.9 | 62.9 |
| Ethanol | 27 | 27 | 27 | 27 |
| Isostearyl glyceryl ether | 0.1 | 0.1 | 0.1 | 0.1 |

TABLE 5

| Composition (%) | Invention product 9 | Invention product 10 | Invention product 11 | Comparative product 1 |
|---|---|---|---|---|
| Compound (I) | 10 | — | — | — |
| Compound (J) | — | 10 | — | — |
| Compound (K) | — | — | 10 | — |
| 1,3-Butylene glycol | 62.9 | 62.9 | 62.9 | 62.9 |
| Ethanol | 27 | 27 | 27 | 30 |
| Isostearyl glyceryl ether | 0.1 | 0.1 | 0.1 | 0.1 |

TABLE 6

|  | Percutaneous water transpiration inhibition degree | Percutaneous absorption inhibition degree |
|---|---|---|
| Invention product 1 | 1.5 | 2563 |
| Invention product 2 | 1.3 | 1564 |
| Invention product 3 | 1.8 | 2706 |
| Invention product 4 | 1.3 | 2890 |
| Invention product 5 | 1.4 | 1363 |
| Invention product 6 | 1.2 | 1731 |
| Invention product 7 | 1.4 | 1184 |
| Invention product 8 | 1.1 | 1088 |
| Invention product 9 | 0.3 | 532 |
| Invention product 10 | 0.8 | 516 |
| Invention product 11 | 0.9 | 739 |

It has been found that the invention products 1 to 11 are superior to Comparative product 1 in effects of inhibiting percutaneous water transpiration and percutaneous absorption and also superior in skin roughness lessening effects.

Test 2

Compositions for external application according to the present invention (invention products) containing the diamide derivative and having the composition as shown in Tables 7 and 8 were prepared and their percutaneous water transpiration and skin conductance were measured and evaluated by the below-described methods. For comparison, a composition for external application (Comparative Product 2) containing Vaseline, which is known to have high skin occlusive property and is therefore used for external dermatological preparations for medical use or skin cosmetic compositions, was subjected to similar measurement and evaluation. Results are shown in Table 9.

(Testing Method)

Ten normal volunteers were washed at the inside of the forearms (both arms), followed by acetone/ether (1/1) treatment to remove the intercellular lipid of the horny layer to roughen their skin. The composition for external application was applied to the test site twice a day for three days. On the next day after final application, the site was washed. After rest for 20 minutes at room temperature of 20° C. and humidity of 30%, the below-described items were measured and evaluated.

(2) Percutaneous Water Transpiration

The percutaneous water transpiration amount was measured by TEVAMETER. In accordance with the below-described formula, effects for inhibiting percutaneous water transpiration were determined.

Degree of percutaneous water transpiration inhibition by the invention product=percutaneous water transpiration amount of the site to which the base ingredient has been applied−percutaneous water transpiration amount of the site to which the invention product has been applied (g/m²/hr)

(2) Water Content in the Horny Layer

The water content in the horny layer was measured by a skin conductance meter. The higher the conductance, the greater the water content in the horny layer. In accordance with the below-described formula, effects for improving water retaining ability of the horny layer were determined.

Water retaining ability improving degree of the invention product=conductance of the site to which the invention product has been applied−conductance of the site to which the base ingredient has been applied (μS)

TABLE 7

| Composition (%) | Invention product 12 | Invention product 13 | Invention product 14 | Invention product 15 |
|---|---|---|---|---|
| Compound (A) | 5 | — | — | — |
| Compound (C) | — | 5 | — | — |
| Compound (D) | — | — | 5 | — |
| Compound (E) | — | — | — | 5 |
| Squalane | 2 | 2 | 2 | 2 |
| Neopentyl glycol dicaprate | 3 | 3 | 3 | 3 |
| Cetanol | 3 | 3 | 3 | 3 |
| Stearyl alcohol | 2 | 2 | 2 | 2 |
| Polyoxyethylene hydrogenated castor oil (40E.O.) | 1 | 1 | 1 | 1 |
| Polyoxyethylene sorbitan monostearate (20E.O.) | 0.5 | 0.5 | 0.5 | 0.5 |
| Sorbitan monostearate | 2.5 | 2.5 | 2.5 | 2.5 |
| Methyl paraoxybenzoate | 0.3 | 0.3 | 0.3 | 0.3 |
| Water | Balance | Balance | Balance | Balance |

TABLE 8

| Composition (%) | Invention product 16 | Invention product 17 | Comparative Product 2 |
|---|---|---|---|
| Compound (G) | 5 | — | — |
| Compound (K) | — | 5 | — |
| Vaseline | — | — | 5 |
| Squalane | 2 | 2 | 2 |
| Neopentyl glycol dicaprate | 3 | 3 | 3 |
| Cetanol | 3 | 3 | 3 |
| Stearyl alcohol | 2 | 2 | 2 |
| Polyoxyethylene hydrogenated castor oil (40E.O.) | 1 | 1 | 1 |
| Polyoxyethylene sorbitan monostearate (20E.O.) | 0.5 | 0.5 | 0.5 |
| Sorbitan monostearate | 2.5 | 2.5 | 2.5 |
| Methyl paraoxybenzoate | 0.3 | 0.3 | 0.3 |
| Water | Balance | Balance | Balance |

TABLE 9

|  | Inhibition degree of percutaneous water transpiration | Water retaining ability improving degree |
|---|---|---|
| Invention product 12 | 2.2 | 4.7 |
| Invention product 13 | 2.8 | 5.6 |
| Invention product 14 | 2.1 | 4.0 |
| Invention product 15 | 2.2 | 5.2 |
| Invention product 16 | 2.0 | 4.1 |
| Invention product 17 | 1.3 | 3.7 |
| Comparative Product 2 | 0.6 | 0.1 |

It has been found that the invention products 12 to 17 were superior to the comparative product 2 in effects for increasing the water content in the horny layer, percutaneous water transpiration inhibiting effects and skin roughness remedial effects.

Test 3

Compositions for external application according to the present invention (invention products) having the compositions shown in Tables 10 to 12 were prepared and their percutaneous water transpiration, skin conductance and skin roughness were evaluated. For comparison, a Vaseline-containing composition for external application (comparative product 2) was subjected the similar evaluation. Results are shown in Tables 11 and 13.

(Testing Method)

(1) Percutaneous Water Transpiration
It was evaluated in a similar manner to Test 2.
(2) Water Content in the Horny Layer
It was evaluated in a similar manner to Test 2.
(3) Score of Skin Roughness
Skin roughness was visually observed and ranked in accordance with the below-described standards. The score was indicated by an average value.

0: No skin roughness is observed.
1: Slight skin roughness is observed.
2: Skin roughness is observed.
3: Rather severe skin roughness is observed.

TABLE 11

|  | Inhibition degree of percutaneous water transpiration | Score of skin roughness |
| --- | --- | --- |
| Invention product 13 | 2.8 | 1.6 |
| Invention product 18 | 3.3 | 1.2 |
| Invention product 19 | 3.2 | 1.3 |
| Invention product 20 | 3.4 | 1.1 |
| Invention product 21 | 2.9 | 1.6 |
| Invention product 22 | 4.5 | 0.3 |
| Invention product 23 | 3.9 | 0.5 |
| Invention product 24 | 3.5 | 0.9 |
| Invention product 25 | 4.2 | 0.4 |
| Invention product 26 | 4.1 | 0.4 |
| Comparative product 2 | 0.6 | 2.7 |

The invention products 13 and 18 to 26 were superior to Comparative Product 2 in effects for inhibiting percutaneous water transpiration from the horny layer and skin roughness remedial effects.

TABLE 10

|  | Invention Products | | | | | | | | | | Comp. Product 2 |
| --- | --- | --- | --- | --- | --- | --- | --- | --- | --- | --- | --- |
|  | 13 | 18 | 19 | 20 | 21 | 22 | 23 | 24 | 25 | 26 | 2 |
| Diamide compound (C) | 5 | 5 | 5 | 5 | 5 | 5 | 5 | 5 | 5 | 5 | — |
| Ceramide II (product of sederma) | — | 0.5 | — | — | — | 0.5 | 0.5 | 0.5 | 0.5 | 0.5 | — |
| Ceramide III (product of cosmoferm) | — | — | 0.5 | — | — | — | — | — | — | — | — |
| Sofcareceramide Kao (Jap. Pat. Laid-Open No. Sho 62-228048) | — | — | — | 0.5 | — | — | — | — | — | — | — |
| Sphingoglycolipid (Kibun Food Chemifa Co., Ltd.) | — | — | — | — | 0.5 | — | — | — | — | — | — |
| Phytosphingosine | — | — | — | — | — | 0.5 | — | — | — | — | — |
| Palmitic acid | — | — | — | — | — | — | 0.5 | — | — | — | — |
| Sunflower oil | — | — | — | — | — | — | — | 0.5 | — | — | — |
| Cholesterol | — | — | — | — | — | — | — | — | 0.5 | — | — |
| Cholesteryl isostearate | — | — | — | — | — | — | — | — | — | 0.5 | — |
| Vaseline | — | — | — | — | — | — | — | — | — | — | 5 |
| Squalane | 2 | 2 | 2 | 2 | 2 | — | 2 | 2 | 2 | 2 | 2 |
| Neopentyl glycol dicaprate | 3 | 3 | 3 | 3 | 3 | 3 | 3 | 3 | 3 | 3 | 3 |
| Cetanol | 3 | 3 | 3 | 3 | 3 | 3 | 3 | 3 | 3 | 3 | 3 |
| Stearyl alcohol | 2 | 2 | 2 | 2 | 2 | 2 | 2 | 2 | 2 | 2 | 2 |
| Polyoxyethylene hydrogenated castor oil (40E.O.) | 1 | 1 | 1 | 1 | 1 | 1 | 1 | 1 | 1 | 1 | 1 |
| Polyoxyethylene sorbitan monostearate (20E.O.) | 0.5 | 0.5 | 0.5 | 0.5 | 0.5 | 0.5 | 0.5 | 0.5 | 0.5 | 0.5 | 0.5 |
| Sorbitan monostearate | 2.5 | 2.5 | 2.5 | 2.5 | 2.5 | 2.5 | 2.5 | 2.5 | 2.5 | 2.5 | 2.5 |
| Methyl paraoxybenzoate | 0.3 | 0.3 | 0.3 | 0.3 | 0.3 | 0.3 | 0.3 | 0.3 | 0.3 | 0.3 | 0.3 |
| Water | Balance | Balance | Balance | Balance | Balance | Balance | Balance | Balance | Balance | Balance | Balance |

TABLE 12

| | Invention products | | | | | | | | Comp. Product |
|---|---|---|---|---|---|---|---|---|---|
| | 13 | 27 | 28 | 29 | 30 | 31 | 32 | 33 | 2 |
| Diamide compound (C) | 5 | 5 | 5 | 5 | 5 | 5 | 5 | 5 | — |
| Glycerin | — | 0.5 | — | — | — | — | — | — | — |
| 1,3-Butylene glycol | — | — | 0.5 | — | — | — | — | — | — |
| Eucalyptus extract (Ichimaru Pharcos Co., Ltd.) | — | — | — | 0.5 | — | — | — | — | — |
| Ginger extract (Maruzen Pharmaceuticals Co., Ltd.) | — | — | — | — | 0.5 | — | — | — | — |
| Sodium lactate | — | — | — | — | — | 0.5 | — | — | — |
| Sodium aspartate | — | — | — | — | — | — | 0.5 | — | — |
| Trimethylglycine | — | — | — | — | — | — | — | 0.5 | — |
| Vaseline | — | — | — | — | — | — | — | — | 5 |
| Squalane | 2 | 2 | 2 | 2 | 2 | 2 | 2 | 2 | 2 |
| Neopentyl glycol dicaprate | 3 | 3 | 3 | 3 | 3 | 3 | 3 | 3 | 3 |
| Cetanol | 3 | 3 | 3 | 3 | 3 | 3 | 3 | 3 | 3 |
| Stearyl alcohol | 2 | 2 | 2 | 2 | 2 | 2 | 2 | 2 | 2 |
| Polyoxyethylene hydrogenated castor oil (40E.O.) | 1 | 1 | 1 | 1 | 1 | 1 | 1 | 1 | 1 |
| Polyoxyethylene sorbitan monostearate (20E.O.) | 0.5 | 0.5 | 0.5 | 0.5 | 0.5 | 0.5 | 0.5 | 0.5 | 0.5 |
| Sorbitan monostearate | 2.5 | 2.5 | 2.5 | 2.5 | 2.5 | 2.5 | 2.5 | 2.5 | 2.5 |
| Methyl paraoxybenzoate | 0.3 | 0.3 | 0.3 | 0.3 | 0.3 | 0.3 | 0.3 | 0.3 | 0.3 |
| Water | Balance | Balance | Balance | Balance | Balance | Balance | Balance | Balance | Balance |

TABLE 13

| | Water retaining ability improving degree | Score of skin roughness |
|---|---|---|
| Invention product 13 | 5.6 | 1.6 |
| Invention product 27 | 7.0 | 1.3 |
| Invention product 28 | 6.1 | 1.4 |
| Invention product 29 | 8.8 | 0.7 |
| Invention product 30 | 8.5 | 0.7 |
| Invention product 31 | 7.9 | 1.0 |
| Invention product 32 | 7.5 | 1.1 |
| Invention product 33 | 8.1 | 0.9 |
| Comparative product 2 | 0.1 | 2.7 |

The invention products 13 and 27 to 33 were superior to Comparative Product 2 in effects for increasing the water content in the horny layer and skin roughness remedial effects.

Test 4

Hair rinses of the present invention (invention products) containing the diamide derivatives and having the compositions as listed in Tables 14 and 15 were prepared and excessive dryness and touch feel of the hair after treated with the resulting hair rinses were evaluated by a panel of 5 experts in accordance with the below-described criteria. The results are shown in Tables 16 and 17.

−2: Bad
−1: slightly bad
0: neither good nor bad
+1: Slightly good
+2: Good

TABLE 14

| Composition (%) | Invention product 34 | Invention Product 35 | Invention Product 36 |
|---|---|---|---|
| Distearyl dimethylammonium chloride | 2 | 2 | 2 |
| Propylene glycol | 3 | 3 | 3 |
| Compound (A) | 1 | — | — |
| Compound (C) | — | 1 | — |
| Compound (D) | — | — | 1 |
| Water | Balance | Balance | Balance |

TABLE 15

| Composition (%) | Invention product 37 | Invention Product 38 | Comparative Product 3 |
|---|---|---|---|
| Distearyl dimethylammonium chloride | 2 | 2 | 2 |
| Propylene glycol | 3 | 3 | 3 |
| Compound (E) | 1 | — | — |
| Compound (G) | — | 1 | — |
| Water | Balance | Balance | Balance |

TABLE 16

| Evaluation items | Invention product 34 | Invention product 35 | Invention product 36 |
|---|---|---|---|
| Excessive dryness of the hair | +1.8 | +1.8 | +1.2 |
| Favorable touch feel | +1.6 | +2.0 | +1.6 |

TABLE 17

| Evaluation items | Invention product 37 | Invention product 38 | Comparative Product 3 |
|---|---|---|---|
| Excessive dryness of the hair | +1.6 | +1.6 | −1.2 |
| Favorable touch feel | +1.6 | +1.8 | −1.0 |

The invention products 34 to 38 were superior to Comparative product 3 in the effects of alleviating excessive hair dryness and improving the touch feel of the hair.

Example 1

A skin lotion having the composition shown in Table 18 was prepared in a conventional manner. The resulting hair lotion exhibited excellent effects for preventing or remedying skin roughness. Compounds (A), (C), (D), (E), (G) and (K) were excellent in miscibility and mixing stability.

TABLE 18

| (Composition) | (%) |
|---|---|
| Compound (A), (C), (D), (E), (G) or (K) | 1.0 |
| Glycerin monostearate | 1.0 |
| Propylene glycol | 4.0 |
| Isopropyl palmitate | 3.0 |
| Lanolin | 1.0 |
| Methyl paraoxybenzoate | 0.1 |
| Perfume | Trace |
| Colorant | Trace |
| Water | Balance |

Example 2

An O/W cream having the composition shown in Table 19 was prepared in a conventional manner. The resulting O/W cream exhibited excellent effects for preventing or remedying skin roughness. Compounds (A), (C), (D), (E), (G) and (K) were excellent in miscibility and mixing stability.

TABLE 19

| (Composition) | (%) |
|---|---|
| Compound (A), (C), (D), (E), (G) or (K) | 3.5 |
| Squalane | 2.0 |
| Neopentyl glycol dicaprate | 3.0 |
| Cetostearyl alcohol | 3.0 |
| Polyoxyethylene sorbitan monostearate (20E.O.) | 2.1 |
| Sorbitan monostearate | 0.9 |
| Polyoxyethylene hydrogenated castor oil (40E.O.) | 1.0 |
| Isostearyl glyceryl ether | 0.2 |
| Ceramide 2 | 0.5 |
| 86% Glycerin | 5.0 |
| Methyl paraoxybenzoate | 0.3 |
| Water | Balance |

Example 3

A shampoo having the composition as shown in Table 20 was prepared in a conventional manner. This shampoo improved the touch feel of the hair and prevented • remedied the roughened skin of the scalp. Compound (A), (C), (D), (E), (G) and (K) were excellent in miscibility and mixing stability.

TABLE 20

| (Composition) | (%) |
|---|---|
| Polyoxyethylene (25) lauryl ether sulfate sodium salt | 15.0 |
| Coconut oil fatty acid diethanolamide | 3.0 |
| Compound (A), (C), (D), (E), (G) or (K) | 2.0 |
| Perfume | 0.5 |
| Colorant | Trace |
| Citric acid | Trace |
| Water | Balance |

Example 4

A hair liquid composition having the composition shown in Table 21 was prepared in a conventional manner. The resulting hair liquid composition imparted the hair with excellent style retention and manageability and good touch feel. Compounds (A), (C), (D), (E), (G) and (K) were excellent in miscibility and mixing stability.

TABLE 21

| (Composition) | (%) |
|---|---|
| Compound (A), (C), (D), (E), (G) or (K) | 1.0 |
| Polyoxypropylene (30) butyl ether | 15.0 |
| Ethanol | 40.0 |
| Water | Balance |
| Perfume | 0.3 |

Example 5

A night cream having the composition as described below was prepared. The resulting night cream was effective for recovering a deterioration in the barrier functions of the skin horny layer and reinforcing the functions, heightened the water retaining ability of the horny layer and exhibited skin roughness preventive • remedial effects. Compounds (A), (C), (D), (E), (G) and (K) were excellent in miscibility and mixing stability.

TABLE 22

| (Composition) | (%) |
|---|---|
| Diamide compound (A), (C), (D), (E), (G) or (K) | 10.0 |
| Ceramide 2 (Takasago International Corp.) | 1.0 |
| Bovine brain lipid (Q.P. Corp.) | 0.5 |
| Sofcare ceramide SLE (Kao Corp.) | 3.0 |
| Macadamia nut oil fatty acid cholesterol (Nippon Fine Chemical Co., Ltd.) | 2.0 |
| Dimethylpolysiloxane 10 cSt | 5.0 |
| Polyether-modified silicone | 2.0 |
| Polyoxyethylene hydrogenated castor oil | 1.0 |
| Cyclic silicone | 7.0 |
| Glycerin | 5.0 |
| Magnesium sulfate | 0.5 |
| Nicotinic amide | 0.2 |
| Dipotassium glycyrrhizinate | 0.1 |
| Amur cork tree extract (Ichimaru Pharcos Co., Ltd.) | 0.1 |
| Heavy liquid isoparaffin | 0.5 |
| Polyvinyl alcohol | 0.3 |
| Methyl paraoxybenzoate | q.s. |
| Perfume | q.s. |
| Purified water | Balance |

Example 6

A sunscreen emulsion having the below-described composition was prepared. The sunscreen emulsion thus obtained was effective for recovering a deterioration in barrier functions of the skin horny layer and reinforcing the function, heightened water retaining ability of the horny layer and exhibited skin roughness preventive • remedial effects. Compounds (A), (C), (D), (E), (G) and (K) were each excellent in miscibility and mixing stability.

TABLE 23

| (Composition) | (%) |
|---|---|
| Diamide compound (A), (C), (D), (E), (G) or (K) | 3.0 |
| Cetyloxypropylglyceryl methoxypropyl myristamide (Example 1 of Japanese Patent Laid-Open No. Hei 08-319263) | 1.0 |
| Phytosphingosine (product of cosmoferm) | 0.1 |
| Stearic acid | 0.2 |
| Palmitic acid | 0.3 |
| Lanoline fatty acid cholesterol | 0.5 |
| 2-Ethylhexyl p-methoxycinnamate | 5.0 |
| Silicon-coated titanium dioxide | 7.0 |
| Silicon-coated zinc oxide | 3.0 |
| Polyether-modified silicone | 2.0 |
| Alkyl-modified silicone | 2.0 |
| Cyclic silicone | 15.0 |
| Sodium silicate | 1.0 |
| Glycerin | 2.0 |
| Dipropylene glycol | 3.0 |
| Kitin | 1.0 |
| Cysteine | 0.2 |
| Burnet extract (Maruzen Pharmaceutical Co., Ltd.) | 0.3 |
| Stearyl glycyrrhizinate | 0.2 |
| Methyl paraoxybenzoate | q.s. |
| Perfume | q.s. |
| Purified water | Balance |

INDUSTRIAL APPLICABILITY

Diamide derivatives (I) of the present invention penetrate into the lipid layer between horny cells, thereby exerting effects of improving (maintaining • reinforcing) water retention capacity and barrier functions of the horny layer or penetrate into the hair, thereby heightening hair protecting effects and at the same time, they have good solubility and excellent stability in a base ingredient. The compositions for external application, humectants and skin barrier function reinforcing agents according to the present invention therefore exhibit effects in prevention treatment of chapping, anti-aging of the skin, improvement in the touch feel of the hair, and prevention and remedy of the chapping of the scalp and are useful as pharmaceuticals, cosmetics or quasi-drugs excellent in stability. The compositions for external application according to the present invention can be prepared efficiently at a low cost.

The invention claimed is:

1. A composition for external application, which comprises a diamide derivative represented by the following formula (1):

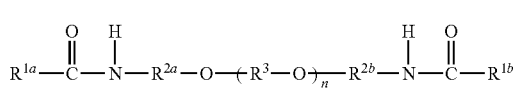

(wherein, $R^{1a}$ and $R^{1b}$ are the same or different and each represents a linear $C_{1-23}$ alkyl or $C_{2-23}$ alkenyl group, $R^{2a}$ and $R^{2b}$ are the same or different and each represents a divalent $C_{1-6}$ hydrocarbon group, $R^3$s are the same or different and each represents a divalent $C_{2-6}$ hydrocarbon group and n stands for 1 to 100).

2. A composition for external application, which comprises a diamide derivative represented by the following formula (1):

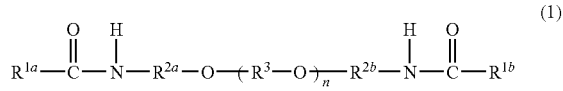

(wherein, $R^{1a}$ and $R^{1b}$ are the same or different and each represents a linear $C_{1-23}$ alkyl or $C_{2-23}$ alkenyl group, $R^{2a}$ and $R^{2b}$ are the same or different and each represents a divalent $C_{1-6}$ hydrocarbon group, $R^3$s are the same or different and each represents a divalent $C_{2-6}$ hydrocarbon group and n stands for 1 to 100) and an intercellular lipid component of the horny layer.

3. A composition for external application according to claim 2 wherein the intracellular lipid component of the horny layer is at least one member selected from the group consisting of ceramides, pseudoceramids, sphingoglycolipids, sphingophospholipids, sphingosines and derivatives thereof, sphinganines and derivatives thereof, higher fatty acids and cholesterols and derivatives thereof.

4. A humectant, which comprises as an effective ingredient, a diamide derivative represented by the following formula (1):

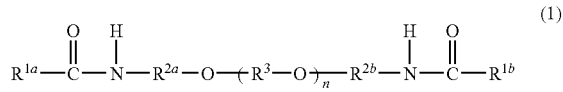

(wherein, $R^{1a}$ and $R^{1b}$ are the same or different and each represents a linear $C_{1-23}$ alkyl or $C_{2-23}$ alkenyl group, $R^{2a}$ and $R^{2b}$ are the same or different and each represents a divalent $C_{1-6}$ hydrocarbon group, $R^3$s are the same or different and each represents a divalent $C_{2-6}$ hydrocarbon group and n stands for 1 to 100).

5. A skin barrier function reinforcing agent, which comprises as an effective ingredient, a diamide derivative represented by the following formula (1):

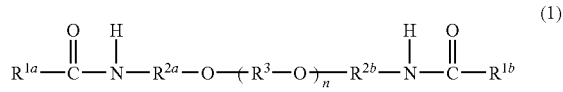

(wherein, $R^{1a}$ and $R^{1b}$ are the same or different and each represents a linear $C_{1-23}$ alkyl or $C_{2-23}$ alkenyl group, $R^{2a}$ and $R^{2b}$ are the same or different and each represents a divalent $C_{1-6}$ hydrocarbon group, $R^3$s are the same or different and each represents a divalent $C_{2-6}$ hydrocarbon group and n stands for 1 to 100).

6. The composition of claim 1, further comprises an oily base.

7. The composition claim 6, wherein said oily base is at least one member selected from the group consisting of vegetable oils, animal oils, synthetic oils, fatty acids, natural glycerides and synthetic glycerides.

8. The composition of claim 1, which comprises 0.001 to 5 wt. % of said diamide.

9. The composition of claim 8, further comprising an anionic surfactant.

10. The composition of claim 9, wherein said anionic surfactant is present in an amount of 5 to 30 wt. %.

11. The composition of claim 1, which comprises 0.1 to 20 wt. % of said diamide.

12. The composition of claim 11, further comprising at least one surfactant selected from the group consisting of cationic surfactant and non-ionic surfactant.

13. The composition of claim 12, wherein said surfactant is present in an amount of 0.1 to 50 wt. %.

14. The composition of claim 1, wherein said composition comprises 0.01 to 5 wt. % of said diamide.

15. The composition of claim 14, wherein said composition further comprises a nonionic surfactant.

16. The composition of claim 15, wherein said nonionic surfactant is present in an amount of 0.01 to 20 wt. %.

17. A composition for external application, which comprises a diamide derivative represented by the following formula (1):

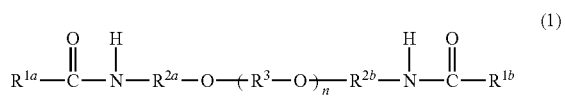
(1)

(wherein, $R^{1a}$ and $R^{1b}$ are the same or different and each represents a $C_{1-23}$ hydrocarbon group, $R^{2a}$ and $R^{2b}$ are the same or different and each represents a divalent $C_{1-6}$ hydrocarbon group, $R^3$s are the same or different and each represents a divalent $C_{2-6}$ hydrocarbon group and n stands for 1 to 100); and a non-ionic surfactant wherein said diamide derivative is represented by the following formula (C):

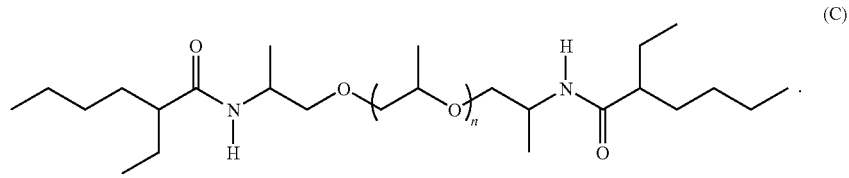
(C)

Average n = 1.7

18. The composition of claim 17, further comprising an intercellular lipid component of the horny layer.

19. A composition for external application according to claim 18 wherein the intracellular lipid component of the horny layer is at least one member selected from the group consisting of ceramides, pseudoceramids, sphingoglycolipids, sphingophospholipids, sphingosines and derivatives thereof, sphinganines and derivatives thereof higher fatty acids and cholesterols and derivatives thereof.

20. The composition of claim 17, further comprises an oily base.

21. The composition claim 20, wherein said oily base is at least one member selected from the group consisting of vegetable oils, animal oils, synthetic oils, fatty acids, natural glycerides and synthetic glycerides.

22. The composition of claim 17, which comprises 0.1 to 20 wt. % of said diamide.

23. The composition of claim 22, further comprising a cationic surfactant.

24. The composition of claim 23, wherein said surfactant is present in an amount of 0.1 to 50 wt. %.

25. The composition of claim 17, wherein said nonionic surfactant is present in an amount of 0.01 to 20 wt. %.

26. A composition for external application, which comprises a diamide derivative represented by the following formula (1):

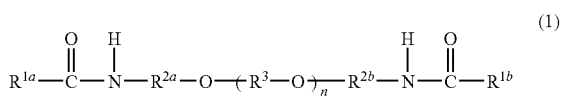
(1)

(wherein, $R^{1a}$ and $R^{1b}$ are the same or different and each represents a $C_{1-23}$ hydrocarbon group, $R^{2a}$ and $R^{2b}$ are the same or different and each represents a divalent $C_{1-6}$ hydrocarbon group, $R^3$s are the same or different and each represents a divalent $C_{2-6}$ hydrocarbon group and n stands for 1 to 100); and an organic acid or salt thereof wherein said diamide derivative is represented by the following formula (C):

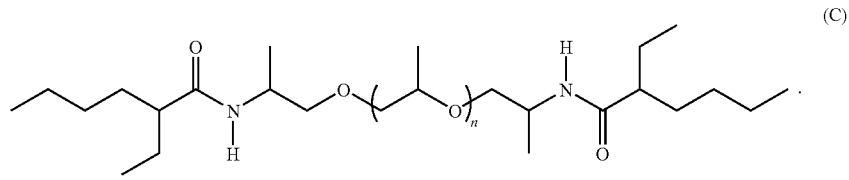
(C)

Average n = 1.7

27. The composition of claim 26, further comprising an intercellular lipid component of the horny layer.

28. A composition for external application according to claim 27 wherein the intracellular lipid component of the horny layer is at least one member selected from the group consisting of ceramides, pseudoceramids, sphingoglycolipids, sphingophospholipids, sphingosines and derivatives thereof, sphinganines and derivatives thereof, higher fatty acids and cholesterols and derivatives thereof.

29. The composition of claim 26, further comprises an oily base.

30. The composition claim 29, wherein said oily base is at least one member selected from the group consisting of vegetable oils, animal oils, synthetic oils, fatty acids, natural glycerides and synthetic glycerides.

31. The composition of claim 26, which comprises 0.001 to 5 wt. % of said diamide.

32. The composition of claim 31, further comprising an anionic surfactant.

33. The composition of claim 32, wherein said anionic surfactant is present in an amount of 5 to 30 wt. %.

34. The composition of claim 26, which comprises 0.1 to 20 wt. % of said diamide.

35. The composition of claim 34, further comprising at least one surfactant selected from the group consisting of cationic surfactant and non-ionic surfactant.

36. The composition of claim 35, wherein said surfactant is present in an amount of 0.1 to 50 wt. %.

37. The composition of claim 26, wherein said composition comprises 0.01 to 5 wt. % of said diamide.

38. The composition of claim 37, wherein said composition further comprises a nonionic surfactant.

39. The composition of claim 38, wherein said nonionic surfactant is present in an amount of 0.01 to 20 wt. %.

\* \* \* \* \*